United States Patent
Fox et al.

(10) Patent No.: US 6,599,509 B2
(45) Date of Patent: *Jul. 29, 2003

(54) COMPOSITIONS AND METHODS COMPRISING HELICOBACTER ANTIGENS FOR TREATMENT AND PREVENTION OF INFLAMMATORY BOWEL DISEASE

(75) Inventors: James J. Fox, Harvard, MA (US); Adrian Lee, Lane Cove (AU); Mark Whary, Pepperell, MA (US); David Schauer, Newton, MA (US)

(73) Assignee: Massachusetts Institute of Technology, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/143,166

(22) Filed: Aug. 28, 1998

(65) Prior Publication Data

US 2002/0044938 A1 Apr. 18, 2002

Related U.S. Application Data

(60) Provisional application No. 60/057,428, filed on Sep. 2, 1997.

(51) Int. Cl.[7] ............................................. A61K 39/02
(52) U.S. Cl. ............................... 424/234.1; 424/252.1; 424/184.1; 424/85.2; 424/85.4; 424/203.1; 435/7.24; 435/184
(58) Field of Search ........................ 424/234.1, 252.1, 424/85.4, 85.2, 184.1, 203.1; 435/7.24, 184.1

(56) References Cited

U.S. PATENT DOCUMENTS

| | | | |
|---|---|---|---|
| 5,260,057 A | | 11/1993 | Cordle et al. ............... 424/85.8 |
| 5,262,156 A | * | 11/1993 | Alemohammad ............ 424/92 |
| 5,368,854 A | * | 11/1994 | Rennick .................... 424/85.2 |
| 5,538,729 A | | 7/1996 | Czinn et al. ............. 424/234.1 |
| 5,610,060 A | | 3/1997 | Ward et al. ............... 435/252.1 |
| 5,830,675 A | * | 11/1998 | Targan et al. ............. 435/7.24 |
| 5,871,749 A | * | 2/1999 | Doidge et al. ........... 424/234.1 |
| 5,985,631 A | * | 11/1999 | Soman et al. ............... 435/184 |

FOREIGN PATENT DOCUMENTS

| | | |
|---|---|---|
| WO | 93/20843 | 10/1993 |
| WO | 95/03824 | 2/1995 |
| WO | 95/22563 | 8/1995 |
| WO | 95/22987 | 8/1995 |
| WO | 95/33482 | * 12/1995 |
| WO | 96/01272 | 1/1996 |
| WO | 96/25430 | 8/1996 |
| WO | 96/33220 | 10/1996 |
| WO | 96/33732 | 10/1996 |
| WO | 96/40893 | * 12/1996 |
| WO | 97/03360 | 1/1997 |
| WO | 97/12910 | 4/1997 |

OTHER PUBLICATIONS

Andus, T et al, Hepato-gastroenterology, Jan.-Feb. 2000, vol. 47(31), pp. 29-43.*
Cahill, RJ et al, Infection Immunity, vol. 65(8), pp. 3126-3131, Aug. 1997.*
D'Inca, R et al, Digestive diseases and sciences, May 1988, vol. 43(5), pp. 988-992. May, 1998.*
Halme, L et al, Journal of Clinical Pathology, vol. 49(1) a pp. 65-67, Jan. 1996.*
Herz, R et al, Scandinavian Journal of Gastroenterology, May 1999, vol. 34(5), pp. 471-473.*
Kucharzik, T et al, Clinical and Experimental Immunology, vol. 100(3), pp. 452-456, Jun. 1995.*
Livingston, RS et al, Journal of Clinical Microbiology, May 1997, vol. 35(5), pp. 1236-1238.*
Mayer, D et al, Gastroenterology, vol. 110(4), Apr. 1996, p. A960.*
Saunders, KE et al, Journal of Clinical Microbiology, vol. 37(1), pp. 146-151, Jan. 1999.*
Wagtmans, MJ et al, Scandinavian journal of Gastroenterology, vol. 32(7), pp. 712-718, Jul. 1997.*
Ward, JM et al, Lab Animal Science, vol. 46(1), pp. 15-20, Feb. 1996.*
Yang, X et al, Journal of Immunology, vol. 16292), pp. 1010-1017, Jan. 15, 1999.*
Macdermott, RP et al, Advances in Immunology, vol. 42, pp. 285-328, 1988.*
Fiocchi, C et al, Immunological Investigations, vol. 18(1-4), pp. 91-102, 1989.*
Brynskov, J et al, New England Journal of Medicine, vol. 321(13), Sep. 28, 1989, pp. 845-850.*
Podolsky, DK et al, Gastroenterology, vol. 88, pp. 20-25, Colonic Mucin composition in primates, 1985.*
Madara, JL et al, Gastroenterology, vol. 88, pp. 13-19, 1985.*
Dielman, LA et al, Gastroenterology, vol. 114(4 of part 2), pp. A965, Apr. 15, 1998(abstract).*
Kullberg, MC et al;, Infection Immunity, vol. 66(11), pp. 5157-5166, Nov. 1998 (abstract).*
Sartor, RB, Gastroenterology clinics of North America, vol. 24(3), pp. 475-507, Sep. 1995.*
Wakefield, AJ et al, Gastroenterology, vol. 108(3), Mar. 1995, pp. 911-916, (abstract).*
Maehlen, J et al, Tidsskr Nor Laegeforen, Sep. 1997, vol. 117(22), pp. 3262-3263, (abstract).*

(List continued on next page.)

*Primary Examiner*—Lynette R. F. Smith
*Assistant Examiner*—Ginny AllenPortner
(74) *Attorney, Agent, or Firm*—Medlen & Carroll, LLP

(57) ABSTRACT

The treatment of IBD in mammals, including humans, is described. More particularly, the present invention relates to compositions and methods for the treatment of IBD associated with Helicobacter or other bacterial infections in mammals, including humans, and to vaccine compositions and antibodies suitable for use in such treatment.

25 Claims, No Drawings

OTHER PUBLICATIONS

Braegger, CP, ACTA Paediatr. suppl. (Norway), Apr. 1994, vol. 83(395), pp. 18–21 (abstract).*

Macpherson, A et al, Gut, Mar. 1996, vol. 38(3), pp. 365–375, (abstract).*

Heap, K et al, Microb. Ecol. Health Dis, vol. 4, abstract S119, Oct. 7–10, 1991.*

Dunkley, ML et al, Microb. Ecol. Health Dis. vol. 4(spec. issue), p. S148, abstract, Oct. 7–10, 1991.*

Chen, M et al, Gastroenterology, vol. 104(14), Apr. 1993, p. 681, col. 1, bottom of col., abstract only.*

Monath, TP et al, American Journal of Gastroneterology, vol. 89, p. 1383, abstract No. 393, Aug. 1994.*

Varga Laszlo et al, Kazuisztika, pp. 359–361, Issue 6, 1992, *Helicobacter pylori* allergia, (English translation) 1992.*

Tomb, JF et al, Nature, vol. 388, pp. 539–547, Aug. 1997.*

James, SP et al, Aliment Pharmacol. Ther. vol. 10(suppl. 2), pp. 1–9, (abstract) 1996.*

Duchmann, R et al, Eur. J. Immunol., Apr. 1996, vol. 26(4), pp. 934–936, 1995.*

Cahill et al, Gastroenterology, vol. 110 (4 suppl), p. A875, 1996.*

Mayer, D et al, Gastroenterology, vol. 110 (4) Apr., p. 960, 1996.*

Cahill et al, Gut, vol. 39, (Suppl. 2) p. A78, abstract No. 3B:123, 1996.*

Halme et al, Gut, Mar. 1996, vol. 38(3), pp. 379–383, Mar.*

Ruuska, T. et al, Journal of Pediatric Gastroenterology and Nutrition, Aug. 1994, vol. 19(2), pp. 181–186,(abstract).*

Foltz, C.J. et al, Laboratory Animal Science, vol. 46(2), pp. 193–197, (abstract), 1996.*

Czinn et al, Infection and Innumity, pp. 2359–2363, 1991.*

Czinn et al, Vaccine, vol. 11 (6), pp. 637–638, 1993.*

Pappo et al, Infection and Immunity, Apr. 1995, pp. 1246–1252, vol. 63(4).*

Cuenca et al, Gastroenterology, vol. 110, pp. 1770–1775, 1996.*

Davin, C et al, Gastroenterology, vol. 104(4), Apr., p. A1035, (abstract) 1993.*

Corthesy–Theulaz et al, Gastroenterology, vol. 109, pp. 115–121, 1995.*

"Cecil's Textbook of Medicine" Eds. Wyngaarden and Smith, W.B. Saunders Co.: 1985.

The Merck Manual of Diagnosis and Therapy. Merck Sharp & Dohme Research Laboratories: 1982.

"Harrison's Principles of Internal Medicine", 12th Ed. McGraw–Hill, Inc.: 1991.

"Inflammatory Bowel Disease", Eds. Kirsner, J.B. et al. 3rd ed Philadelphia:Lea and Febiger, 1988.

"Digestive Diseases And Sciences", Ed. Zipser, R.D., 33 Suppl.: 1S–87S: 1988.

Engstrand, L. "Potential Animal Models of *Helicobacter pylori* Infection In Immunological And Vaccine Research," *FEMS Immunology and Medical Microbiology* 10:265–270, 1995.

Ferrero, R. et al., "Local Immunoglobulin G Antibodies In The Stomach May Contribute To Immunity Against *Helicobacter* Infection In Mice," *Gastroenterology* 112:185–194, 1997.

Lee and Chen, "Successful Immunication Against Gastric Infection With *Helicobacter* Species: Use Of A Cholera Toxin B–Subunit–Whole–Cell Vaccine," *Infection and Immunity* 3594–3597, Aug. 1994.

Weltzin, et al., "Generation Of Systemic And Mucosal Antibody Responses By Repeated Intranasal Immunization Without Adjuvant," *FASEB* 9:A216, 1995.

Weltzin, et al., "Novel Intranasal Immunization Techniques For Antibody Induction And Protection Of Mice Against Gastric *Helicobacter felis* Infection," *Vaccine* 15:370–376, 1997.

* cited by examiner

COMPOSITIONS AND METHODS COMPRISING HELICOBACTER ANTIGENS FOR TREATMENT AND PREVENTION OF INFLAMMATORY BOWEL DISEASE

This application for patent under 35 U.S.C. 111(a) claims priority to Provisional Application Serial No. 60/057,428 filed Sep. 2, 1997 under 35 U.S.C. 111(b).

This invention was made with government support under NIH-R01-CA67529 and N01-CO-5600 awarded by NIH. The government has certain in the invention.

FIELD OF THE INVENTION

The present invention relates to the treatment of Inflammatory Bowel Disease in mammals, including humans. More particularly, the present invention relates to immunogens and immunization with bacterial antigens, including but not limited to Helicobacter antigens, to prevent or treat Inflammatory Bowel Disease.

BACKGROUND OF THE INVENTION

Inflammatory Bowel Disease (IBD) refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia (e.g. iron deficiency anemia and anemia of chronic disease or of chronic inflammation).

The etiology (or etiologies) and pathogenesis of IBD are still unclear. Previous understanding of the pathogenesis was limited to a three-stage process: (a) an irritant, which could be an immune process or infectious agent, activates (b) leukocytes which release enzymes such as proteases and inflammatory mediators such as histamine, serotonin and prostaglandins, and (c) these products cause edema, pain, heat and loss of function. See Wyngaarden and Smith (eds.) Cecil's Textbook of Medicine (W. B. Saunders Co. 1985), Berkow (ed.). The Merck Manual of Diagnosis and Therapy (Merck Sharp & Dohme Research Laboratories, 1982), and Harrison's Principles of Internal Medicine, 12th Ed., McGraw-Hill, Inc. (1991).

Numerous theories implicate multiple factors leading up to IBD including genetic predisposition, environmental factors, infectious agents and immunologic alterations. See Kirsner, J. B., et al. (eds), Inflammatory Bowel Disease, 3rd ed., Lea and Febiger, Philadelphia (1988); Zipser, R. D., (ed.), Dig. Dis. Sci., 33 Suppl.:1S-87S (1988). The immunologic alterations in IBD appear to be autoimmune in nature, with colonic autoantibodies and lymphocyte-cytotoxicity directed against colonic epithelial cells. However, even the latest developments in the immunologic aspects of the pathogenesis of IBD cannot answer the basic question, i.e., whether the detected changes in humoral and cellular immunity reflect a primary defect or secondary response to injury.

Treatment for IBD currently includes steroids, sulphasalazine and its derivatives, and immunosuppressive drugs such as cyclosporin A, mercaptopurine and azathioprine. Such therapies are directed toward suppression of the general immune response. Such an approach often results in poor success, has little or no selectivity, and can be accompanied by unwanted and sometimes dangerous consequential side effects.

Thus, there exists a need for effective treatment, both prophylactic and curative, for IBD. Such a therapy should be specific and should not be accompanied by unwanted side effects.

SUMMARY OF THE INVENTION

The present invention relates to the treatment of Inflammatory Bowel Disease (IBD) in mammals, including humans. More particularly, the present invention relates to immunogens and immunization with antigens expressed by Helicobacter as well as other bacteria (e.g. organisms considered to be normal resident flora and organisms known to be pathogenic) to prevent or treat Inflammatory Bowel Disease.

The present invention contemplates both passive immunization and active immunization. Where passive immunization is employed, antibodies to bacterial antigens (e.g. Helicobacter antigens) are made in one host (e.g. goats, horses, chickens, rabbits, etc.) and administered to a host having symptoms of (or at risk for) inflammatory bowel disease. In a preferred embodiment, active immunization is employed and a host is immunized directly with a bacterial antigen (e.g. Helicobacter antigen) preparation, in order to achieve a protective immune response. While it is not essential to the use of the present invention to understand the precise mechanism by which a therapeutic benefit is achieved, it is believed that immunization with such antigens result in the normalization of cytokine Th1/Th2 levels and/or the consequent production of antibodies which are protective against acute infection by microorganisms causing IBD.

According to one aspect of the present invention, there is provided a method of eliciting in a mammalian host a protective immune response to Helicobacter-associated IBD. This method comprises orally administering to the host an immunogenically effective amount of *Helicobacter hepaticus* antigen preparation to elicit the desired protective immune response.

According to another aspect of the present invention, there is provided a vaccine composition comprising an amount of said Helicobacter antigen preparation, effective to elicit a protective response in a human patient, in association with a pharmaceutically acceptable adjuvant.

In addition, there is provided a vaccine composition comprising an amount of bacterial antigens isolated from a bacteria other than Helicobacter, effective to elicit a protective response in a human patient.

In one embodiment, the present invention contemplates a method, comprising a) providing i) a host having symptoms of inflammatory bowel disease and ii) a source of bacterial antigens (e.g. Helicobacter antigens); b) orally administering to the host an effective amount of said bacterial antigen to elicit an immune response. In another embodiment, the present invention contemplates a method, comprising a) providing i) a host at risk for inflammatory bowel disease and ii) a source of bacterial antigens (e.g. Helicobacter antigens); b) orally administering to the host an effective amount of said bacterial antigen to elicit an immune response. All animal hosts are contemplated, including humans.

It is not intended that the invention be limited by the species of bacteria or by the source of antigen. In a preferred embodiment, the source of antigen is selected from the group consisting of inactivated whole organisms, whole cell lysates and purified bacterial antigen. It is also not intended that the present invention be limited by the means of inactivating whole organisms or the means of preparing cell lysates. In one embodiment, the whole organisms are inactivated by formalin or gamma irradiation. In another embodiment, the cell lysates are prepared with SDS and/or proteinase K.

It is also not intended that the antigen preparation be limited to antigen alone. In a preferred embodiment, antigen is administered with adjuvant, and in particular a mucosal adjuvant. In one embodiment, the mucosal adjuvant is selected from the group consisting of cholera toxin and heat labile enterotoxin of *Escherichia coli*. The antigen(s) may be administered in a preparation where the antigen is in association with a pharmaceutically acceptable carrier or diluent.

A variety of Helicobacter species are contemplated as sources of antigen, including but not limited to *H. fenelliae, H. cinaedi, H. pullorum, H. rappini* and *H. muridarum*. In a preferred embodiment, the Helicobacter species is selected from the group consisting of *Helicobacter hepaticus* and *Helicobacter bilis*. The different species (such as *Helicobacter hepaticus*) are conveniently cultured for preparation of antigen as described in U.S. Pat. No. 5,610,060 which issued Mar. 3, 1997, the entire contents of which are hereby incorporated by reference. Other sources of antigens include any pathogens or members of the normal flora shown to contribute to the induction of IBD.

GENERAL DESCRIPTION OF THE INVENTION

Recent findings indicate that Inflammatory Bowel Disease is a consequence of the colonization of the intestinal mucus by populations specially adapted to this site which can induce a severe inflammatory response if other conditions are present. While an understanding of the precise series of steps leading to disease is not necessary to the successful practice of the present invention, it is believed that IBD requires as a predisposing factor a major perturbation in the intestinal ecosystem such that the balance of the mucus associated flora changes, thereby allowing surface associated bacteria with increased inflammatory potential to become permanently established. Experimental evidence in mice suggests that the surface associated bacteria inducing IBD are members of the non-gastric helicobacters such as *H. hepaticus* and *H. bilis*. Where the rate of translocation of non-gastric helicobacters increases or the host's mucosal environment changes to become more reactive to helicobacter antigens, these normally intestinally located bacteria can become lodged in the liver and induce hepatitis. In certain cases, due to the nature of the bacteria involved and the reactivity of the host to them, these lesions appear to correlate with IBD.

It is further believed that the normal immune response to the normal mucus-adapted intestinal bacteria is a non-inflammatory Type2/Th2 mediated response which restricts colonization and maintains a balance between host and parasite. When this balance is altered due to an ecological change in the mucus-associated flora or acquisition of a new bacterium colonizing the lower bowel surface, the immune reactions to the bacteria in the mucus layer switches to a non-effective Th1 response. This potent inflammatory response is destructive to the intestinal tissue and leads to IBD.

In the present invention, a new therapeutic modality for inflammatory bowel disease is described which has not hitherto been considered. Oral immunization of patients with symptoms of inflammatory bowel disease (IBD) is contemplated with relevant antigens of the mucus-associated microbiota or luminal bacteria, (e.g. *Helicobacter hepaticus* and *Helicobacter bilis*, that have colonized the large bowel surface together with an appropriate adjuvant such as modified cholera toxin (CT) or the heat labile enterotoxin of *Escherichia coli* (LT). Oral immunization with the appropriate combination of antigen and adjuvant will therefore result in resolution of the symptoms of IBD and be an effective therapy for this disease.

It will be appreciated, however, that the present invention is not limited to the treatment of IBD. Thus, the present invention also includes within its scope the treatment or prophylaxis of mammals, including humans, for *H. hepaticus* infection, wherein the patient is orally immunized with an immunologically effective amount of *H. hepaticus* antigen in order to elicit protective immune responses, including the formation of protective antibodies to the *H. hepaticus* pathogen. Preferably, the *H. hepaticus* is administered in association with a mucosal adjuvant, for example cholera toxin.

Moreover, the present invention includes within its scope, the passive immunization of mammals, including humans, against infection. This is achieved by orally administering an effective amount of a *H. hepaticus* specific antibody (or antibodies to other bacterial antigens) to the patient. Preferably a *H. hepaticus* specific IgA monoclonal antibody is orally administered to the patient. In another embodiment, a polyclonal antibody is administered.

The vaccine of the present invention is administered orally in amounts readily determined by persons of ordinary skill in the art. Thus, for adults, a suitable dosage would be in the range of 10 $\mu$g to 10 mg, more specifically 50 $\mu$g to 5 mg. Similar dosage ranges would be applicable for children.

As noted above, a suitable mucosal adjuvant is cholera toxin. Others which may be used are non-toxic derivatives of cholera toxin, including its B subunit and/or conjugates of antigen plus cholera toxin or its B subunit, microcapsules, or immune stimulating complexes (ISCOM's) or liposomes and attenuated live vectors such as viruses or Salmonella bacteria. The amount of mucosal adjuvant employed depends on the type of mucosal adjuvant used. For example, when the mucosal adjuvant is cholera toxin, it is suitably used in an amount of 5 $\mu$g to 50 $\mu$g, more specifically 10 $\mu$g to 35 $\mu$g. When used in the form of microcapsules, the amount used will depend on the amount employed in the matrix of the microcapsule to achieve the desired dosage. Suitable carriers and diluents are enteric coated capsules and/or 0.2N NaHCO$_3$ and/or saline.

Experimental

The nonpathogenic antigen of this invention can be used in the construction of a vaccine comprising an immunogenic amount of *H. hepaticus* antigen (or other bacterial antigen) and a pharmaceutically acceptable carrier. This antigen can be killed or modified live bacteria or immunogenic fragments of the organisms. Alternatively, mixtures of intact nonpathogenic bacteria and immunogenic fragments can be used. The vaccine can then be used in a method of preventing infection in a subject by administering the vaccine to the subject.

The use of a purified antigen (or purified antigens) from *H. hepaticus* or other bacteria is contemplated. As used herein, "purified" means the antigen is separated from some (but not necessarily all) other bacterial and cellular contaminants. An antigenic fragment can be isolated from the whole antigen by chemical or mechanical disruption. The purified fragments thus obtained can be tested to determine their immunoreactivity and specificity by routine methods. Antigenic fragments of the antigen can also be synthesized directly. An immunoreactive fragment is defined as an amino acid sequence of at least about 5 consecutive amino acids derived from the antigen amino acid sequence.

Alternatively, a protein moiety of *H. hepaticus* or other bacteria can be obtained by treating the whole organism with an ionic detergent such as sodium dodecyl sulfate or a nonionic detergent such as Triton X-100 or ethylphenyl-polyethylene glycol (NP-40, Shell Oil Company). The protein fragments so obtained can be tested for immunoreactivity and specificity by ELISA.

Finally, the antigenically specific determinant of this invention can be obtained by synthesizing a vector comprising a nucleic acid sequence encoding an antigenically specific determinant of *H. hepaticus* or other bacteria. The vector can then be placed in a host wherein the antigenically specific determinant will be synthesized. The selection of a nucleic acid sequence that encodes an antigenically specific determinant can be accomplished by screening clone libraries of *H. hepaticus* DNA (or other bacterial DNA). Briefly, the bacterium is lysed and the DNA extracted via standard procedure using 1% sodium dodecyl sulfate and proteinase K. The resulting DNA is then partially digested with restriction endonuclease EcoRI, size fractionated and gel purified (agarose gel electrophoresis), and cloned into lambda phage vector lambda zapII following standard procedures. The recombinant plaques are screened for antigen production via ELISA with primary antibody being human or other non-human (e.g., mouse) convalescent sera absorbed with an *E. coli* lysate. Antigen expressing clones are subcloned.

The subclones expressing *H. hepaticus* specific antigens (or other bacterial antigens) are sequenced and corresponding synthetic peptides are constructed from the deduced amino acid sequence for use as diagnostic antigens or immunogens. Alternatively, recombinant antigens could be purified by affinity chromatography or high pressure liquid chromatography and the like. The antigen to be used in the vaccine can be tested to determine its protective ability and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human, a guinea pig or a mouse, the condition of the subject, the size of the subject, etc. Thereafter, an animal so inoculated with the antigen can be exposed to the bacterium to test the protective effect of the specific immunogenic fragment. The specificity of a putative immunogenic fragment can be ascertained by testing sera, other fluids or lymphocytes from the inoculated animal for cross reactivity with other closely related bacteria.

The pharmaceutically acceptable carrier in the vaccine of the instant invention can comprise saline or other suitable carriers. An adjuvant can also be a part of the carrier of the vaccine, in which case it can be selected by standard criteria based on the particular antigen used, the mode of administration and the subject. Methods of administration can be by oral or sublingual means, or by injection, depending on the particular vaccine used and the subject to whom it is administered.

It can be appreciated from the above that the vaccine can be used as a prophylactic or a therapeutic. Thus, subjects with the disease can be treated utilizing the vaccine. Further, through such vaccination the onset of disease can be prevented.

What is claimed is:

1. A method for treating inflammatory bowel disease, comprising:
    a) providing: i) a host having symptoms of inflammatory bowel disease and ii) a composition comprising inactivated whole organisms or whole cell lysates of an organism selected from the group consisting of *H. fenelliae, H. cinaedi, H. pullorum, H. rappini, H. muridarum, H. hepaticus,* and *H. bilis;*
    b) orally administering to said host an effective amount of said composition so as to elicit an immune response, and ameliorate said symptoms of inflammatory bowel disease.

2. The method of claim 1, wherein said host is a mammal.

3. The method of claim 2, wherein said mammal is a human.

4. The method of claim 1, wherein said composition further comprises adjuvant.

5. The method of claim 4, wherein said adjuvant comprises mucosal adjuvant.

6. The method of claim 5, wherein said mucosal adjuvant is selected from the group consisting of cholera toxin and heat labile enterotoxin of *Escherichia coli.*

7. A method for preventing inflammatory bowel disease, comprising:
    a) providing: i) a host at risk for inflammatory bowel disease and ii) a composition comprising inactivated whole organisms or whole cell lysates of an organism selected from the group consisting of *H. fenelliae, H. cinaedi, H. pullorum, H. rappini, H. muridarum, H. hepaticus,* and *H. bilis;* and
    b) orally administering to said host an effective amount of said composition so as to elicit an immune response, and prevent said host from experiencing symptoms of inflammatory bowel disease.

8. The method of claim 7, wherein said host is a human.

9. The method of claim 7, wherein said composition further comprises adjuvant.

10. The method of claim 9, wherein said adjuvant comprises mucosal adjuvant.

11. The method of claim 10, wherein said mucosal adjuvant is selected from the group consisting of cholera toxin and heat labile enterotoxin of *Escherichia coli.*

12. A method for treating inflammatory bowel disease, comprising:
    a) providing: i) a host having symptoms of inflammatory bowel disease and ii) a composition comprising an adjuvant and inactivated whole organisms or whole cell lysates of an organism selected from the group consisting of *H. fenelliae, H. cinaedi, H. pullorum, H. rappini, H. muridarum, H. hepaticus,* and *H. bilis;* and
    b) orally administering to said host an amount of said composition so as to elicit an immune response, and ameliorate said symptoms of inflammatory bowel disease.

13. The method of claim 12 wherein said adjuvant comprises cholera toxin.

14. The method of claim 12 wherein said symptoms comprises rectal prolapse.

15. A method for preventing inflammatory bowel disease, comprising:
    a) providing: i) a host at risk for inflammatory bowel disease and ii) a composition comprising an adjuvant and inactivated whole organisms or whole cell lysates of an organism selected from the group consisting of *H. fenelliae, H. cinaedi, H. pullorum, H. rappini, H. muridarum, H. hepaticus,* and *H. bilis;* and b) orally administering to said host an effective amount of said composition so as to elicit an immune response, and prevent said host from experiencing symptoms of inflammatory bowel disease.

16. The method of claim 15 wherein said adjuvant comprises cholera toxin.

17. The method of claim 15 wherein said symptoms comprises rectal prolapse.

18. A method for treating inflammatory bowel disease, comprising:
   a) providing: i) a host having symptoms of inflammatory bowel disease and ii) a composition comprising inactivated whole organisms or whole cell lysates of an organism selected from the group consisting of *H. fenelliae, H. cinaedi, H. pullorum, H. rappini, H. muridarum, H. hepaticus,* and *H. bilis*; and
   b) orally administering to said host an amount of said composition so as to elicit an immune response, and ameliorate said symptoms of inflammatory bowel disease wherein said symptoms comprise rectal prolapse.

19. The method of claim 18, wherein said inactivated whole organisms or whole cell lysates of a sonicate of said organisms.

20. The method of claim 18, wherein said composition comprises a sonicate of Helicobacter bacteria and a mucosal adjuvant.

21. The method of claim 20, wherein said mucosal adjuvant comprises cholera toxin.

22. A method for treating inflammatory bowel disease, comprising:
   a) providing: i) a host having symptoms of inflammatory bowel disease and ii) a composition consisting of inactivated whole organisms or whole cell lysates of *H. bilis, H. hepaticus, H. muridarum, H. rodentium,* or *H. trogontum,* and;
   b) orally administering to said host an amount of said composition so as to elicit an immune response, and ameliorate said symptoms of inflammatory bowel disease.

23. A method for preventing inflammatory bowel disease, comprising:
   a) providing: i) a host at risk for inflammatory bowel disease and ii) a composition consisting of inactivated whole organisms or whole cell lysates of *H. bilis, H. hepaticus, H. muridarum, H. rodentium,* or *H. trogontum,* and;
   b) orally administering to said host an effective amount of said composition so as to elicit an immune response, and prevent said host from experiencing symptoms of inflammatory bowel disease.

24. A method for treating inflammatory bowel disease, comprising:
   a) providing: i) a host having symptoms of inflammatory bowel disease and ii) a composition a composition consisting of inactivated whole organisms or whole cell lysates of *H. bilis, H. hepaticus, H. muridarum, H. rodentium,* or *H. trogontum,* and;
   b) orally administering to said host an amount of said composition so as to elicit an immune response, and ameliorate said symptoms of inflammatory bowel disease wherein the symptoms comprise rectal prolapse.

25. A method for preventing inflammatory bowel disease, comprising:
   a) providing: i) a host at risk for inflammatory bowel disease and ii) a composition consisting of an adjuvant and inactivated whole organisms or whole cell lysates of *H. bilis, H. hepaticus, H. muridarum, H. rodentium,* or *H. trogontum;* and
   b) orally administering to said host an amount of said composition so as to elicit an immune response, and ameliorate said symptoms of inflammatory bowel disease wherein said symptoms comprise rectal prolapse.

* * * * *

UNITED STATES PATENT AND TRADEMARK OFFICE
CERTIFICATE OF CORRECTION

PATENT NO. : 6,599,509 B2
DATED : September 22, 2003
INVENTOR(S) : James J. Fox et al.

It is certified that error appears in the above-identified patent and that said Letters Patent is hereby corrected as shown below:

Title page,
Item [75], Inventors, "James Fox's" middle initial should be -- G -- instead of "J".

Signed and Sealed this

Eighth Day of June, 2004

JON W. DUDAS
*Acting Director of the United States Patent and Trademark Office*